United States Patent
Thompson et al.

(10) Patent No.: US 9,615,745 B2
(45) Date of Patent: Apr. 11, 2017

(54) SYSTEM AND METHOD FOR WIRELESS BIOSENSOR MONITORING

(75) Inventors: Christopher C. Thompson, Needham, MA (US); Robert Westervelt, Lexington, MA (US); Alex Nemiroski, Cambridge, MA (US); Keith L. Obstein, Nashville, TN (US)

(73) Assignee: The Brigham and Women's Hospital, Boston, MA (US)

( * ) Notice: Subject to any disclaimer, the term of this patent is extended or adjusted under 35 U.S.C. 154(b) by 1137 days.

(21) Appl. No.: 13/511,580

(22) PCT Filed: Nov. 24, 2010

(86) PCT No.: PCT/US2010/058061
§ 371 (c)(1),
(2), (4) Date: Sep. 20, 2012

(87) PCT Pub. No.: WO2011/066431
PCT Pub. Date: Jun. 3, 2011

(65) Prior Publication Data
US 2013/0018235 A1    Jan. 17, 2013

Related U.S. Application Data

(60) Provisional application No. 61/264,548, filed on Nov. 25, 2009.

(51) Int. Cl.
*A61B 5/07* (2006.01)
*A61B 5/00* (2006.01)
(Continued)

(52) U.S. Cl.
CPC ............ *A61B 5/0002* (2013.01); *A61B 5/076* (2013.01); *A61B 5/14539* (2013.01);
(Continued)

(58) Field of Classification Search
CPC ..... A61B 5/0002; A61B 5/076; A61B 5/6882; A61B 5/14539; A61B 5/14551; A61B 5/036
(Continued)

(56) References Cited

U.S. PATENT DOCUMENTS 6,682,490 B2 * 1/2004 Roy et al. ............... 600/486
6,711,423 B2 * 3/2004 Colvin, Jr. ........... A61B 5/0031
128/899

(Continued)

OTHER PUBLICATIONS

The International Search Report and Written Opinion as mailed on Jul. 27, 2011 for International Application No. PCT/US2010/058061.

*Primary Examiner* — Tiffany Weston
(74) *Attorney, Agent, or Firm* — Quarles & Brady LLP

(57) ABSTRACT

A system and method for monitoring a physical parameter of a subject is provided. The system may include a casing with a sensor coupled to the casing. The sensor may be configured to detect a physical parameter of the subject. The physical parameter may include a chemical parameter of the subject. The system includes an endoscopic clip coupled to the casing and may include a wireless transmitter for transmitting a signal via a wireless medium. The signal encodes the physical parameter of the subject detected by the sensor and the wireless transmitter is electronically connected to the endoscopic clip. The system may further include a monitor configured to communicate with the wireless transmitter for receiving the signal encoding the physical parameter of the subject.

6 Claims, 5 Drawing Sheets

(51) Int. Cl.
   *A61B 5/145*     (2006.01)
   *A61B 5/03*      (2006.01)
   *A61B 5/1455*    (2006.01)

(52) U.S. Cl.
   CPC ............ *A61B 5/6882* (2013.01); *A61B 5/036* (2013.01); *A61B 5/14551* (2013.01)

(58) Field of Classification Search
   USPC .......................... 600/302, 101, 109, 117–118
   See application file for complete search history.

(56) References Cited

U.S. PATENT DOCUMENTS

| | | | |
|---|---|---|---|
| 2002/0042562 A1* | 4/2002 | Meron et al. ................. | 600/361 |
| 2003/0167000 A1* | 9/2003 | Mullick ............. | A61B 1/00087 |
| | | | 600/424 |
| 2006/0167339 A1 | 7/2006 | Gilad et al. | |
| 2008/0046037 A1* | 2/2008 | Haubrich ............. | A61B 5/0028 |
| | | | 607/60 |
| 2008/0146871 A1* | 6/2008 | Arneson et al. ............. | 600/101 |
| 2008/0312502 A1 | 12/2008 | Swain et al. | |
| 2009/0221882 A1 | 9/2009 | Furman | |
| 2009/0299359 A1* | 12/2009 | Swain ................... | A61B 18/08 |
| | | | 606/27 |

* cited by examiner

SYSTEM AND METHOD FOR WIRELESS BIOSENSOR MONITORING

CROSS-REFERENCE TO RELATED APPLICATIONS

This application represents the U.S. National Stage of International Application No. PCT/US2010/058061, filed Nov. 24, 2010 which claims priority to U.S. Provisional Patent Application Ser. No. 61/264,548 filed on Nov. 25, 2009, and entitled "WIRELESS BIOSENSOR WITH FASTENING CLIP." The foregoing applications are incorporated herein by reference in their-entirety.

STATEMENT REGARDING FEDERALLY SPONSORED RESEARCH

This invention was made with government support under 5 U54 CA119349-03 awarded by the National Institutes of Health. The government has certain rights in the invention.

BACKGROUND OF THE INVENTION

The field of the invention is wireless biosensor devices. More particularly, the invention relates to wireless biosensor devices that include a fastening clip for mounting the wireless biosensor within a subject.

Although in vivo wireless biosensors were first deployed for wireless pH monitoring in the 1990's, the ultimate impact of these devices on the medical community has only been marginal. Because prior electronics, radio, and energy storage technologies were relatively inefficient, existing wireless biosensors tend to be large devices with simple communications capabilities and are not generally preferred over traditional medical equipment. Advances in microelectronics and telecommunications over the past two decades have ushered in an era of small, self-contained electronic devices with the capability for sensing, computing, and wireless communication. The market-driven need for increased complexity, functionality, and interoperability, as well as the decreased size and cost of wireless devices, has recently led to a series of technological developments aimed at creating entire systems contained in a few, or even a single CMOS chip. This theme of convergence has created miniature devices with the functionality needed to create a new breed of wireless biosensors with the small size, intelligence, and autonomy needed for practical medical applications.

Advances in electronics have recently led to wearable, implantable, and ingestible sensor devices that are commercially available. The technology presents one opportunity to begin providing a realistic alternative to traditional medical procedures that can be relatively costly, invasive, uncomfortable, and time-consuming. By simplifying the procedures for monitoring, diagnostics, and testing, while providing continuous access to patient data, these biosensor devices stand to revolutionize the medical industry in the near future.

The physical size of recently developed biosensor devices limits their potential applications. Some of the smallest devices created, for example, having a minimum dimension of approximately 1 cm, have been used to image the gastrointestinal (GI) tract. Such devices, however, are only capable of a one-time recording of the state of the GI tract, because they pass through the GI tract in a relatively short time period. The devices cannot be fixed to monitor a specific area over a longer period of time of days or weeks, and are primarily used for diagnosing the general health of the GI tract, rather than monitoring a specific condition at a particular locality of the GI tract.

Fixing the location of a sensor is difficult for sensors in the GI tract. As such, in many cases, doctors return to traditional endoscopy to monitor the GI tract, which allows easy access to the GI tract for observation and tests, and surgery. Although some sensors are configured to be mounted to the GI lining, their mounting mechanisms generally require puncturing of the GI lining, preventing the devices from being used to monitor sensitive areas, such as gastric ulcers or other internal wounds.

Accordingly, there is a need for a sensor system that allows for monitoring of an internal region of a subject over an extended period of time.

SUMMARY OF THE INVENTION

The present invention is wireless biosensor device (WBD). The WBD can be mounted within a gastrointestinal (GI) tract using a fastening clip.

In one configuration, the present invention is a system for monitoring a physical parameter of a subject. The system includes a casing, and a sensor coupled to the casing. The sensor is configured to detect a physical parameter of the subject. The physical parameter may include a chemical parameter of the subject. The system includes an endoscopic clip coupled to the casing.

In another configuration, the present invention is a system for monitoring a physical parameter of a subject. The system includes a casing, and a sensor coupled to the casing. The sensor is configured to detect a physical parameter of the subject. The physical parameter may include a chemical parameter of the subject. The system includes a fastening mechanism coupled to the casing for securing the sensor within a gastrointestinal (GI) tract of the subject.

In one implementation, the WBD is configured to communicate wirelessly with a monitor device mounted to an exterior of a subject.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

The present invention is described in one or more embodiments in the following description with reference to the Figures, in which like numerals represent the same or similar elements. While the invention is described in terms of the best mode for achieving the invention's objectives, it will be appreciated by those skilled in the art that it is intended to cover alternatives, modifications, and equivalents as may be included within the spirit and scope of the invention as defined by the appended claims and their equivalents as supported by the following disclosure and drawings.

The present system provides a Wireless Biosensor Device (WBD) including a fastening clip. The WBD may be configured to be form factor compatible for insertion using an endoscopic clipping device. In some cases the clipping device may comprise an endoscopic having an appropriate attachment for operating the endoscopic clips of the WBD. As such, the WBD may be attached to a surface of the GI tract using an endoscopic clipping device insertion method. Using the endoscopic insertion method, the WBC is first attached to the clipping device. A portion of the clipping device and the attached WBD are then inserted into the subject. The clipping device can be used to facilitate placement of the WBD into the correct region of the subject. At the appropriate location, the clipping device is used to deploy the WBD by fixing it to the appropriate region of the subject.

The WBD may include a radio communications subsystem for communicating with one or more devices located external to the subject. In one implementation, the radio communications subsystem is compliant to the Institute of Electrical and Electronics Engineers (IEEE) 802.15.4 standard (IEEE 802.15.4) providing integration with external networks and other biosensor devices.

Figure 1:
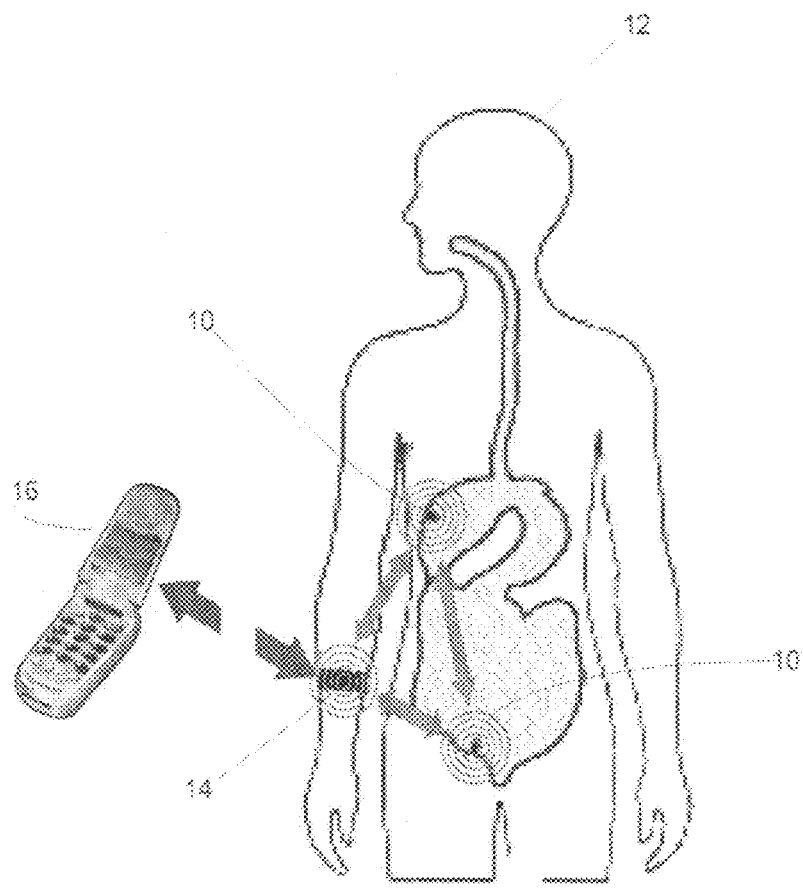
FIG. 1 is an illustration of one implementation of a medical sensor system including a plurality of Wireless Biosensor Devices (WBDs) implanted within a subject.

FIG. 1 is an illustration of one implementation of a medical sensor system including a plurality of WBDs implanted within a subject. WBDs 10 are placed inside the GI tract of a subject 12 and are configured to detect one or more biological condition of subject 12. WBDs 10 may then communicate the biological data describing the condition to monitor 14 through a wireless communication network. Monitor 14 may be mounted on the skin of subject 12 to improve communication between WBDs 10 and monitor 14. Monitor 14 may also be mounted near the skin of subject 12, but will then be subject to significant radio-frequency (RF) interference resulting from the reflection of RF radiation at the skin-air interface of subject 12. Monitor 14 is also configured to communicate with external systems such as cell phone 16 or other computers, servers, or medical personnel to relay data describing a condition of subject 12 or to provide information and/or warnings directly to subject 12 through a communication mechanism such as a visual interface, speaker, or vibration device. For example, in a normal operation, monitor 14 may routine report measurement data to a central computer server for storage an later review by a doctor. Monitor 14 may also be configured to perform a high-level (i.e., somewhat superficial) review of the measurement data to identify one or more danger conditions. If a danger condition is detected, monitor 14 may be configured to both store the measurement data on a computer server, and also alert the subject. To alert the subject, monitor 14 may be configured to communicate with any appropriate user interface device such as a cell phone, television or computer. Alternatively, monitor 14 itself may incorporate a user interface for alerting the subject directly that a danger condition exists.

Figure 2A:
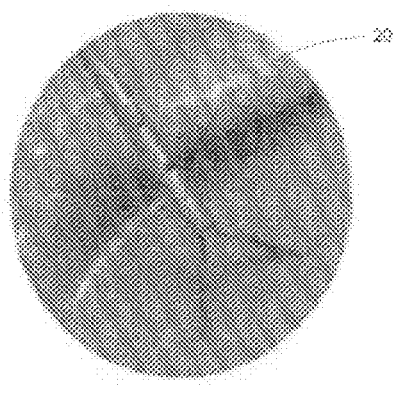
FIGS. 2a and 2b are illustrations of an example endoscopic clip being mounted within the gastrointestinal (GI) tract of a subject.
Figure 2B:
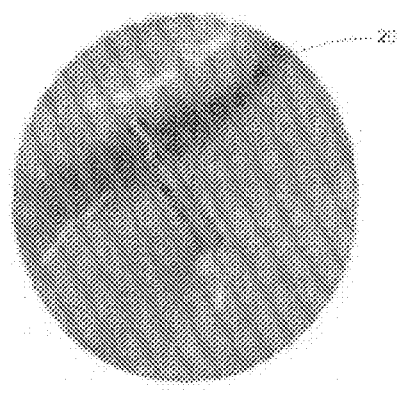

In one implementation, each WBD 10 combines the physical form factor, attachment mechanism, and insertion procedure of an endoscopic clip, with biosensors controlled by microelectronics that communicate with a monitor outside the body. FIGS. 2a and 2b are illustrations of an example endoscopic clip being mounted within the GI tract of a subject. In FIG. 2a, endoscopic clip 20 is shown prior to installation in a surface of the GI tract, while FIG. 2b, illustrates endoscopic clip 20 after installation. The arms of endoscopic clip 20 contact a surface of the GI tract and hold endoscopic clip 20 in place. In various implementations, the WBD may have a minimum dimension on the 3 millimeter (mm)-scale and a form factor consistent with existing endo-clip technology. Using the clips, WBD 10 may be held at a fixed position in the GI tract for an extended period of time (e.g., days to weeks) using the described fastening clip. Alternatively, WBD 10 may be affixed within subject 10 using a fixation loop that may be attached using an off-the-shelf clip structure.

WBD 10 may include various sensor systems including sensors for the measurement of pH, pressure, and/or specific chemicals. An optional optical system for providing both illumination and spectrally filtered detection of scattered light may be included within WBD 10 for direct color detection using RGB filters, sensing of fluorescence from a medical biomarker using an optical filter, or providing other visual analysis functionality. WBD 10 may be configured to implement various sensing methods including pulse oximetry and hemoglobin concentration sensing. In various other implementations, WBD 10 may include an electrical heating system to cauterize internal wounds, or a drug delivery system for the release of therapeutic substances such as Hemostatic powder to treat specific conditions.

WBD 10 includes an ultra-low power microprocessor chip, including, for example, sensor inputs and a flash memory for controlling WBD 10. The microprocessor may be programmed to allow WBD 10 to be configured for a range of applications.

Returning to FIG. 1, the microprocessor of WBD 10 is in communication with monitor 14 located external to the subject. In one implementation, WBD 10 uses a wireless communication protocol to transmit data to monitor 14. Having received the data, monitor 14 may transmit the data to computers or servers that are in communication with monitor 14, or display or otherwise communicate the information to a user of the system (e.g., a patient or doctor that wishes to review the biological data).

In one implementation, monitor 14 allows a user of the system to extract data from one or more WBDs 10, wirelessly control and program WBDs 10, form a network of internal sensors, and connect to existing communication networks (e.g., mobile phone networks, the Internet, etc.) for remote monitoring of patients or for emergency contact with the medical facility.

In one implementation, each monitor 14 acts as a node in a Body Sensor Network (BSN). The monitors may include an antenna attached to a surface of the subject to provide an improved Radio Frequency (RF) connection with the internal WBDs. When communicating, WBDs 10 and monitor 14 may use standard communication protocols to establish wireless network connections between monitors 14 at different locations on the body. In addition, one monitor may act as a router or network controller to relay data generated by each WBD to a medical facility via the Internet, cellular phone network, or other communication network, using a Bluetooth wireless networking protocol, for example.

A BSN with strategically placed WBDs 10 can quickly become an important element in the diagnosis, monitoring, and treatment of a diverse range of gastroenterological problems. For example, a WBD 10 with the appropriate optical filter may be configured to recognize a fluorescent biomarker to identify tagged substances, such as fresh blood or food. After detecting one or more of these potential medical conditions, WBDs 10 may transmit the collected data to monitors 14. Monitors 14, after receiving the data, may alert the patient to the condition, or forward the data to a medical center, doctor or other entity for analysis. In this manner, various medical conditions such as ulcer or wound bleeding can thus be immediately addressed, or the behavior of the stomach can be observed.

These capabilities may have wide reaching applications for the management of various GI medical conditions such as GI bleeding. Depending upon the implementation, the treatment of bleeding ulcers or other wounds may also be possible by cauterizing the wound with a resistive heater of WBD 10, effectively inducing hemostasis. The measurement of pH by WBD 10 may facilitate the detection of drastic changes in acidity that can aid in the monitoring of gastroesophageal reflux disease, help perform a Small Bowel Motility test, or detect gastric fluid or bile leakage. In WBDs 10 that incorporate the required sensors, it may be possible to analyze food intake and content for possible monitoring of Bariatric Surgery candidates. Similarly, WBD 10 may be used for drug monitoring within subject 10. For example, WBD 10 may be used to ensure that appropriate levels of particular drugs are being ingested by subject 10 and to verify that appropriate levels of particular drugs are found within subject 10.

Figure 3:
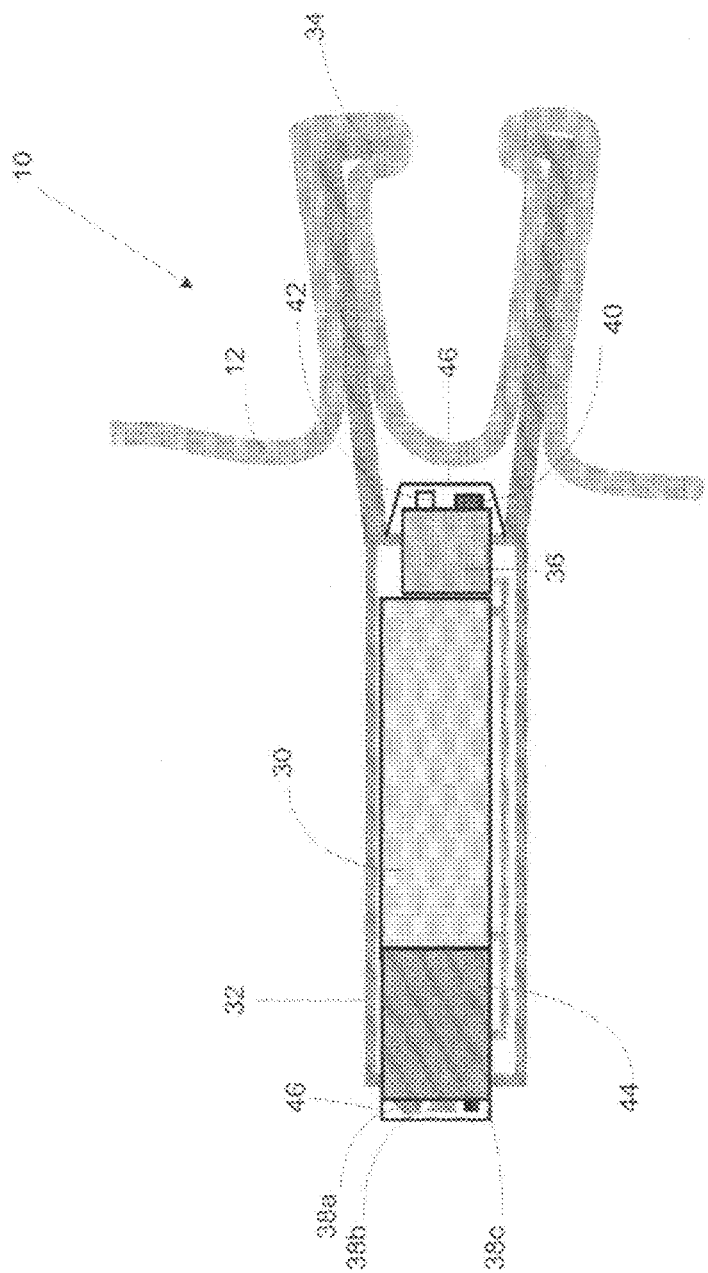
FIG. 3 is a schematic illustration showing various components of a WBD, including a power source and fastening clip.

FIG. 3 is a schematic illustration showing various components of WBD 10, including a power source 30, and fastening clip 34. WBD 10 includes casing 32 to contain and protect several of the components of WBD 10. Casing 32 may include any material that can withstand the GI tract environment such as medical grade metals, plastics, or composites. Casing 32 is attached to fastening clip 34 and allows WBD 10 to be connected to a surface of an internal portion of subject 12. As shown in FIG. 3, fastening clip 34 of WBD 10 may be connected to a surface of the GI tract of subject 12 via one or more gripper arms. In one implementation, fastening clip 34 includes an endoscopic clip, however, other fastening clips may be connected to casing 32 for connecting WBD 10 to subject 12.

Casing 32 contains power source 30 for powering the electronics of WBD 10. Power source 30 is connected to electronic systems 36 and 44 to provide electrical energy and may include a battery, capacitor, or other energy storing or generation device. In some implementations, electronic and sensor system 36 contains the primary electronic and sensor systems for WBD 10, while electronic and sensor systems 44 contain secondary systems. Electronic systems 36 and 44 may include microprocessors, flash memory or other data storage mechanisms, and radio modulation systems for implementing the functionality of WBD 10.

Electronic systems 36 and 44 are each connected to a plurality of sensors. Sensors 38a-38c are connected to electronic system 44 and sensors 40 and 42 are connected to electronic system 36. A protective covering 46 may be disposed over the sensors to provide protection from environmental hazards. Covering 46 includes a material having transparency at particular wavelengths (for example, to allow infrared or visible light waves to pass through) and may include a plastic, glass, or other material suitable for disposition over any of the sensors. In some implementations, covering 46 operates as a filter to only allow light of a particular wavelength band and color to pass through. Covering 46 may include any necessary additives to perform the light-filtering function.

The sensors may include chemical, mechanical, or optical sensors for detecting and measuring one or more biological condition. For example, sensors 40 or 42 may include an optical sensor for directly observing a surface of the GI tract of subject 12 to detect the presence of fresh blood or fluorescent biomarkers used to label various components of blood (such as cells, albumin, or other proteins). WBD 10 may also include a Microelectromechanical System (MEMS) pressure sensor, and a pH sensor. Data collected by each of the sensors may be stored in a memory unit of WBD 10 until accessed by monitor 14 located outside the body or transmitted to monitor 14.

In WBD 10 pressure sensing may be performed by a MEMS pressure sensor. pH measurement can be done through a pH sensitive transistor or a cylindrical hydrogel based pH sensor with capacitive read functionality. The pressure and pH sensors allow WBD 10 to detect various characteristics about its environment that may be used to monitor one or more medical conditions, or characterize the operation of WBD 10.

For example, the pH sensors may be used to detect whether WBD 10 has been dislodged from the WBD 10 original mounting location. If a pH level of fluids surrounding WBD 10 changes significantly, that may indicate WBD 10 has become dislodged. Because the average pH of the stomach and small bowel differ significantly, a drastic change in pH may indicate that WBD 10 has dislodged and passed from the stomach to the small bowel and begun to pass through the rest of the GI tract. Other sensors may be included to sense bicarbonate level or pertinent environmental factors to detect WBD 10 migration from other areas.

In some cases, one or more servos or motors may be connected to the arms of fastening clip 34 and configured to articulate the arms. In the case that WBD 10 detects that it has become disclosed (e.g., because of an accelerated change in PH level), the servos may be used to articulate the arms in an attempt to re-attach fastening clip 34 and WBD 10 to the subject. The servo may be also configured to retract the fastening clip 34 into the WBD 10 itself.

In some implementations, to facilitate re-attachment (or to facilitate initial attachment), WBD 10 may incorporate multiple sets of fastening clips 34 to provide multiple attachment points for WBD 10. In one implementation, WBD 10 incorporates two fastening clips 34 positioned at opposite ends of the WBD 10. The multiple fastening clips 34 may each be of the same design, or may incorporate multiple fastening clip configurations, with some being moveable by a servo, while others are generally fixed.

In the case that WBD 10 incorporates moveable fastening clips, and so can reattach itself within a subject, WBD 10 may be configured to be ingested by a subject. WBD 10 would then be configured to pass through the subject's GI tract. By monitoring its position within the GI tract (e.g., by detecting local pH levels, or by any other appropriate detection mechanism), WBD 10 can be configured to attach to the subject at a pre-determined location. In one such implementation, multiple WBDs 10 could be introduced into a subject's GI tract, with each WBD 10 configured to attach itself to the subject at a different position with the GI tract. In that configuration, the multiple WBDs 10 would then be able to report measurement data throughout a length of the subject's GI tract.

The optical sensors may be implemented by a photonic integrated circuit (PIC) positioned near the tissue at the base of grippers (see, for example, sensors 40 and 42 on FIG. 3). For direct optical detection, light reflected from a pulsed white Light Emitting Diode (LED) mounted to WBD 10 may be monitored by a group of color-filtered photodiodes. The RGB color value of the reflected light and the color of the observed area can thus be determined. The WBD 10 may then transmit the detected color information to monitor 14. Monitor 14 may perform analysis on the color data, or forward the information to another party for analysis.

Alternatively, WBD 10 may be configured to perform optical detection of fluorescent medical biomarker dyes. The dyes, when excited by light of an appropriate wavelength, relax and emit photons at a lower energy. In that case, the optical system may include a colored LED providing the initial biomarker excitation, and adjacent photodiodes, filtered to detect any fluorescence. Multilayer optical filters can be engineered to separate the spectrum of the fluorescence from the LED excitation. In some cases, multiple photodetectors sensitive to different wavelengths detect the peak of the emission spectrum through second derivative analysis. Using these techniques, appropriately tagged substances such as blood or food can be detected and differentiated from untagged substances.

Figure 4:
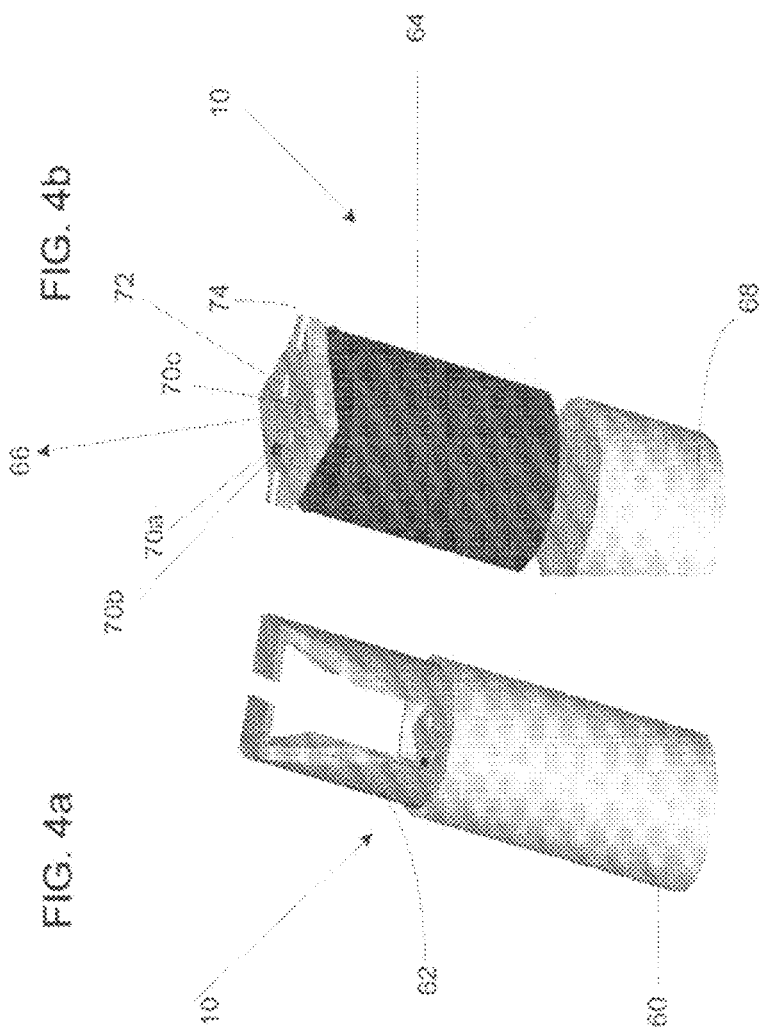
FIGS. 4a and 4b illustrate one specific implementation of a WBD having an LED, a photodiode with an optical filter, a battery and a pH sensor.

FIGS. 4a and 4b illustrate one specific implementation of WBD 10 having a photodiode, battery and pH sensor. FIG. 4a is an illustration of the exterior design of WBD 10, while FIG. 4b is an exploded view of some of the internal components of WBD 10. Referring to FIGS. 4a and 4b, an external casing 60 is connected to clips 62 of WBD 10 for connecting WBD 10 to a surface of the GI tract of a subject. In this example, clips 62 include a conductive material and are connected to the internal circuitry of WBD 10 to act as a dipole antenna to facilitate wireless communications between WBD 10 and monitor 14. The antenna could also be a small integrated unit a few mm in size. For example, commercial antenna are available at 2.5 GHz that are about 1 cm long and a couple of mm in width.

Within WBD 10, power source 64 is connected to a main electronics chip 66. Electronics chip 66 communicates with several sensors to collect data from subject 12 and to transmit that data to monitor 14. As shown in FIG. 4b, electronics chip 66 is connected to pH sensor 68 and filtered diodes 70a-c. An LED 72 is connected to electronic chip 66 for emitting light. Antenna connectors 74 are connected to electronic chip 66. When electronic chip 66 is inserted into casing 60, antenna connectors 74 contact clips 62 and establish an electrical connection between clips 62 and chip 66. Chip 66 may then use clips 62 as an antenna to wirelessly broadcast data to monitor 14, or another device configured to receive transmissions from WBD 10.

In one example use, WBD 10 of FIGS. 4a and 4b may be used to monitor potential gastrointestinal re-bleeding from recently treated wounds such as peptic ulcers. When a blood vessel is eroded by an ulcer, sudden internal bleeding can be fatal. With the aid of an endoscope, the ulcer can be observed and treated by clamping it shut with a clips 62 of WBD 10. After installation, WBD 10 can detect one or more conditions of the ulcer and may remain in the body until the ulcer heals, with WBD 10 naturally detaching and passing through the rest of the GI tract after the ulcer is healed. WBD 10 may also be used to monitor other patient populations, such as those at high risk of bleeding resulting from the use of anticoagulant medications, or varices (e.g., esophageal, gastric, or intestinal varices), and post-surgery patients.

WBD 10 may fixed within the GI tract using clips 62 to detect bleeding from ulcers or other sources in the GI tract. In some cases, WBD 10 may be fixed within the GI tract using a range of attachment mechanisms in addition to a hemostatic clip. The sensor module could be attached using wire arm clips, which simply attach the sensor without stopping bleeding. Alternatively, loops of wire or a suture may be formed within the GI tract and attached to a separate clip formed on a side of the sensor module. In another example, a rubber band may fix the position of WBD 10. Using the rubber band, the GI lining may be drawn through a rigid ring attached to the sensor module, using the vacuum port of an endoscope. An expanded rubber band may then be pushed over the ring by the endoscope to close around the tissue on the far side, fixing the ring and sensor module to the wall of the GI tract.

After installation, and upon a query from monitor 14, WBD 10 awakens from a low power standby mode, activates its sensors, collects data, and relays its findings back to monitor 14. If bleeding is detected and battery power permits, a short pulse of oscillating electrical current may be passed through the clips 62 to cauterize the ulcer. Detection of blood, clip dislodgment, or the results of the cauterizing procedure may be relayed through monitor 14 to other systems to notify relevant medical personnel.

Each WBD 10 may be wirelessly connected to one or more monitors 14 located on the surface of the body of the subject using wireless communication protocols. To connect the BSN to a medical facility, or other external system devices, one or more of monitors 14 may act as a gateway between the BSN and a mobile phone network or the Internet, i.e. through a Bluetooth connection. Each monitor 14 may be further configured to display information or warnings to the patient, such as by flashing an LED or displaying information on an LCD screen. The warnings may also be relayed to a medical facility, along with real-time data by monitors 14 via a suitable communications network.

Each WBD 10 communicates with each monitor 14 using a wireless communications protocol. For example, a first system implementation of WBD 10 includes an ultra-low power RF chip connected to the clips of WBD 10 to generate a radiated signal. Control of the system may be implemented by a low power microprocessor (for example, less than 30 microwatts (μW)). The radio system, microprocessor, and a flash memory subsystem may all be contained, for example, on a single ultra-low power chip, such as the ChipCon CC2430 or the Ember EM250. Power consumption may be reduced to very low levels by keeping WBD 10 in sleep mode until it is awakened by an external query from monitor 14, or another system component. WBD 10 may then transmit short data packets containing the biological data.

In another implementation, WBD 10 may be configured to use Radio Frequency ID (RFID) technology to broadcast biological data to monitor 14. In that case, monitor 14 illuminates WBD 10 with an RF signal. In response, WBD 10 reflects a time-modulated RF signal to monitor 14. The reflected RF signal may be modulated by alternately connecting the two halves of the dipole antenna formed by the clips of WBD 10 using a Field Effect Transistor (FET). Any such modulation of the reflected RF signal may encode data, and, when using an appropriate multiplexing protocol, be read out by monitor 14.

In this case, each WBD 10 consumes only relatively low amounts of power as the RF carrier is generated outside the subject by monitor 14, enhancing battery lifetime of WBD 10. Depending on the antenna geometry and configuration of WBD's 10 power source, it may also be possible to recharge WBD 10 using a similar technique.

In another implementation, WBD 10 includes one or more RFID chips for broadcasting information to monitor 14. Each RFID chip in WBD 10 has the single task of returning its hard-coded ID number upon receiving a radio query. To communicate particular information to monitor 14, for a WBD 10 including two different RFID chips, each having different ID numbers, or a single RFID chip having two ID numbers, WBD 10 may respond to the radio query by broadcasting one of the two ID numbers. In that case, the broadcast of one ID number may signify "OK" while the broadcast of the other ID number may signify "Emergency" (for example, after WBD 10 has detected bleeding or clip dislodging).

Due to the human body's heterogeneity, it may be difficult to make accurate predictions of the RF propagation from an internally-mounted WBD 10 to a monitor 14. The large, frequency dependent dielectric constant of the human body may have significant affect when attempting to match the clip (or antenna) size of WBD 10 with the RF wavelength, and for estimating the attenuation of the RF signal as it passes through the body. In many implementations of the present system, the antenna of WBD 10 includes a commercially manufactured antenna having a length of less than 1 centimeter (cm). In other implementations, the antenna is formed by the two arms of the clip connected to a casing of WBD 10. If the clips are configured as a simple dipole antenna configuration, each arm may be approximately one-half wavelength long. In one implementation, the wavelength is approximately 1 cm.

The dielectric constant of the stomach may be approximately $\in S \approx 68$ to 62 for RF frequencies in the range of 400 MHz to 2.4 GHz with free space wavelengths of 75 cm to 12.5 cm. The free space wavelengths correspond to wavelengths in the stomach of 9.1 cm to 1.6 cm. As such, in one implementation of the present system, the signal carrier frequency is set to approximately 2.4 GHz. At 2.4 GHz, because RF energy is absorbed as it passes through the human body, the power of an isotropically radiated 2.4 GHz signal, detected immediately outside the body (−10 cm away), is attenuated 40 to 60 dB by absorption and by the solid angle covered by the receiving antenna. Further losses may be incurred through imperfect conversion of the electrical to radiated signal at the antenna (insertion loss) and vice versa. Even in view of these losses, however, a strong wireless connection between WBD 10 and monitor 14 may be established. For example, the ChipCon CC2430 chip has RF output power 0.6 dBm (1.15 mW) and a receiver sensitivity of −92 dBm. Assuming 60 dB attenuation of the signal during propagation, a reliable wireless link can be established, with a margin of approximately 30 dB.

Monitors 14 may be placed at convenient locations outside the body on a surface of subject 12. To improve the RF link between monitor 14 and WBD 10, monitors 14 may be attached to the skin of the subject using an adhesive such as an adhesive medical patch, or other mechanical coupling mechanism. Because monitors 14 are generally mounted outside the body, the power consumption of monitor 14 is not a primary concern, unlike the power consumption of WBD 10. As such, monitors 14 may be assigned relatively high-power consumption responsibilities such as supplying a wireless carrier signal for communication, performing a majority of the data analysis, or implementing remote networking.

Using communication protocols, such as the IEEE 802.15.4 standard described below, monitors 14 may form a wireless network that establishes a data connection between a number of WBDs 10 and monitors 14 at different locations around the body. A monitor 14 can also act as a router, to connect the BSN to external system components via a cell phone network, Internet, or other communications network to relay alarms and data to a remotely located medical facility. If many WBDs 10 are scattered throughout the GI tract, multiple WBDs 10 can provide a wireless link between any pair of sensors, no matter the physical distance. Additionally, the collection of monitors 14 located about the body may enable the system to triangulate the position of each WBD 10 by measuring the power of the RF signal of WBD 10 within their wireless reach, which decays via signal attenuation and spreading loss.

In one specific implementation of the present system, each WBD 10 and monitor 14 are configured to implement the IEEE 802.15.4 wireless communication standard for communicating data between each of the WBDs 10 and monitors 14. The standard is oriented towards the implementation of a low cost, ultra-low-powered, long-life wireless sensor network for home automation, remote sensing, energy management, hospital care and telecommunication. One example implementation of the IEEE 802.15.4 standard includes ZigBee as defined by the ZigBee alliance. In some cases, ZigBee technology has been developed and miniaturized to offer a more powerful alternative to RFIDs.

Figure 5:
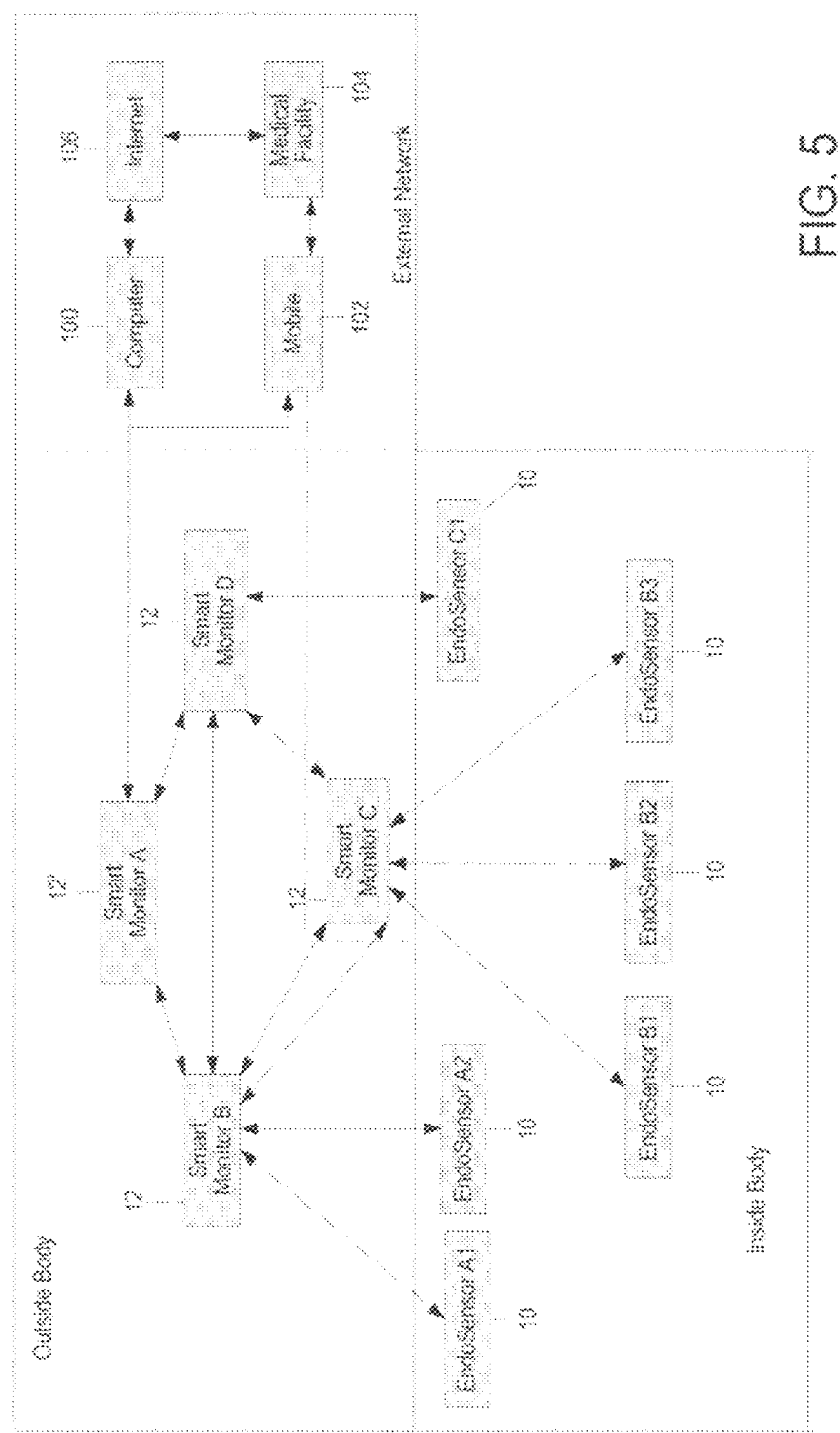
FIG. 5 is an illustration of an example ZigBee-based network tree for implementing one embodiment of the present system.

An example network tree for implementing the present system is illustrated in FIG. 5. The present example network is described in accordance with ZigBee, however other networks operating in accordance with IEEE 802.15.4 or other wireless network standards may be used. Each monitor 14 operates as a router between a WBD 10 star network and other monitors 14, forming a mesh network at the ZigBee Router level. One monitor 14 is designated the ZigBee Coordinator. The Coordinator can communicate with a local computer or mobile phone via a communications network, enabling remote patient monitoring. In some cases, a monitor 14 simultaneously functions as both a Router and Coordinator. As such, the simplest network of a single monitor 14 and single WBD 10 may still enable communication with external networks (e.g., Internet networks or mobile phone networks).

ZigBee networks are comprised of nodes which can have three different roles: ZigBee Coordinator (ZC), ZigBee Router (ZR), and ZigBee End-Device (ZED). Because each ZigBee node can fulfill any of these three roles, the same communication device may be used at each location in the network. The ZED only communicates with its parent ZR, which in turn forms the basis of the ZigBee mesh network, allowing routing of data between any two points in the system. One of the ZR routers will be chosen to function as a ZC, being responsible for the synchronization of all nodes, monitoring network topology, dynamically reconfiguring data paths to reflect the current state of the network, and communicating with external networks, such as a cellular phone network, or a computer connected to the Internet to transmit data.

As shown in FIG. 5, each WBD 10 is a ZED, each monitor 14 is a ZR, and one monitor 14' is made a ZC. The ZC monitor 14' can then communicate data received from each WBD 10 to external system components such as computer 100 or mobile phone 102. Using computer 100, for example, monitor 14' may transmit data to medical facility 104 using Internet 106. Alternatively, monitor 14' may use mobile phone 102 and the network to which mobile phone 102 is connected to transmit data to medical facility 106.

Using the present system, it is possible to install WBD 10 into the GI tract of a subject to monitor one or more conditions throughout the GI tract. The system may be configured to sense bleeding, pH, pressure, bodily fluids tagged by fluorescent biomarkers, and targeted biochemicals. The sensors and electronics can be small enough to be fit inside and be mounted using endoscopic clips and inserted into the body with existing endoscopic installation procedures. An onboard battery or other power source, combined with an programmable ultra-low power microprocessor, flash memory, and RF communication permits WBD 10 to sense, store, and wirelessly transmit data out of the body to external monitors. The monitors enable the sensors to share data and may also analyze the data to alert the patient to a dangerous condition, and alert a medical facility through a cellular phone network or the Internet.

While one or more embodiments of the present invention have been illustrated in detail, the skilled artisan will appreciate that modifications and adaptations to those embodiments may be made without departing from the scope of the present invention as set forth in the following claims.

What is claimed is:

1. A system for monitoring a physical parameter of a subject, the system comprising:
    a casing;
    a sensor coupled to the casing, the sensor being configured to detect a physical parameter of the subject;
    an endoscopic clip coupled to the casing and configured to act as an antenna to facilitate wireless communications from the system; and
    a battery arranged in the casing and wherein the endoscopic clip is coupled to the battery and configured to deliver an electrical current to the subject to cauterize a portion of the subject based on the physical parameter of the subject
    wherein the sensor is connected to the endoscopic clip to transmit information detected about the physical parameter of the subject wirelessly using the endoscopic clip as the antenna.

2. The system of claim 1, wherein the sensor includes a Microelectromechanical System (MEMS) pressure sensor.

3. The system of claim 1, including a wireless transmitter for transmitting a signal encoding the information detected about the physical parameter of the subject and the wireless transmitter connected between the endoscopic clip and the sensor.

4. The system of claim 3, including a monitor configured to communicate with the wireless transmitter for receiving the signal encoding the physical parameter of the subject.

5. The system of claim 1, wherein the sensor includes an optical sensor configured to detect a fluorescence of a medical biomarker using the optical sensor to detect the physical parameter of the subject.

6. The system of claim 1, wherein the sensor is configured to wirelessly communicate with other deployed sensors to form a network of internal sensors and connect to external communication networks to report on detected physical parameters of the subject.

* * * * *